(12) United States Patent
Hayashi et al.

(10) Patent No.: US 11,906,495 B2
(45) Date of Patent: Feb. 20, 2024

(54) SENSOR AND METHOD FOR CALIBRATING SENSOR

(71) Applicant: KABUSHIKI KAISHA TOSHIBA, Tokyo (JP)

(72) Inventors: Yumi Hayashi, Ayase Kanagawa (JP); Hiroaki Yamazaki, Yokohama Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 550 days.

(21) Appl. No.: 16/991,146

(22) Filed: Aug. 12, 2020

(65) Prior Publication Data

US 2021/0109071 A1 Apr. 15, 2021

(30) Foreign Application Priority Data

Oct. 9, 2019 (JP) ................................. 2019-185736

(51) Int. Cl.
*G01N 33/00* (2006.01)

(52) U.S. Cl.
CPC ..... *G01N 33/0006* (2013.01); *G01N 33/0027* (2013.01); *G01N 33/0073* (2013.01)

(58) Field of Classification Search
CPC ............... G01N 33/00; G01N 33/0006; G01N 33/0073; G01N 33/0027
USPC ........................................................ 73/1.06
See application file for complete search history.

(56) References Cited

U.S. PATENT DOCUMENTS

| 10,883,947 | B2 * | 1/2021 | Bao ..................... G01N 25/4873 |
| 2003/0019275 | A1 * | 1/2003 | Lloyd ............... H01M 8/04955 73/1.06 |
| 2003/0182988 | A1 * | 10/2003 | Aldridge ............ G01N 33/0006 73/31.07 |
| 2005/0262924 | A1 * | 12/2005 | Wood .................. G01N 33/0006 73/31.05 |
| 2006/0118416 | A1 * | 6/2006 | Liu ....................... G01N 33/005 204/431 |
| 2006/0266098 | A1 * | 11/2006 | Eickhoff .............. G01N 33/007 73/1.06 |
| 2014/0284188 | A1 * | 9/2014 | Yamazaki ............. B81B 3/0086 438/669 |
| 2015/0253212 | A1 * | 9/2015 | Hayashi ................ G01L 9/0073 438/52 |
| 2015/0262757 | A1 * | 9/2015 | Yamazaki ................ H01G 5/18 361/290 |
| 2015/0292970 | A1 * | 10/2015 | Gando .................... G01L 9/125 29/25.41 |

(Continued)

FOREIGN PATENT DOCUMENTS

| JP | 2007-17208 A | 1/2007 |
| JP | 2014-228447 A | 12/2014 |
| JP | 2019-56607 A | 4/2019 |

*Primary Examiner* — Alexander A Mercado
(74) *Attorney, Agent, or Firm* — Finnegan, Henderson, Farabow, Garrett & Dunner, LLP

(57) ABSTRACT

According to one embodiment, a sensor includes a sensor part including a first film, and a structure body including a second film. The first film has a first density, and a first concentration of a first element. The second film has at least one of a second density, or a second concentration of the first element. The second concentration is greater than the first concentration. The second density is greater than the first density.

15 Claims, 14 Drawing Sheets

(56) References Cited

U.S. PATENT DOCUMENTS

| | | | |
|---|---|---|---|
| 2016/0075550 A1* | 3/2016 | Nakamura | B81B 7/007 |
| | | | 257/415 |
| 2016/0103082 A1* | 4/2016 | Kimura | G01N 25/20 |
| | | | 73/25.01 |
| 2016/0265986 A1* | 9/2016 | Ono | G01L 9/0073 |
| 2016/0265996 A1* | 9/2016 | Hayashi | G01L 19/04 |
| 2017/0016866 A1* | 1/2017 | Chey | G08B 29/22 |
| 2017/0074925 A1* | 3/2017 | Yamazaki | H05B 3/265 |
| 2017/0343522 A1* | 11/2017 | Ikehashi | G01B 7/22 |
| 2019/0086377 A1* | 3/2019 | Ikehashi | G01N 27/221 |
| 2019/0162694 A1* | 5/2019 | Hayashi | G01N 27/4074 |
| 2020/0011828 A1* | 1/2020 | Hayashi | G01N 27/227 |
| 2020/0080954 A1* | 3/2020 | Yamazaki | B81B 7/02 |
| 2020/0300717 A1* | 9/2020 | Masunishi | G01L 19/0092 |
| 2020/0300803 A1* | 9/2020 | Hayashi | G01N 27/4074 |

* cited by examiner

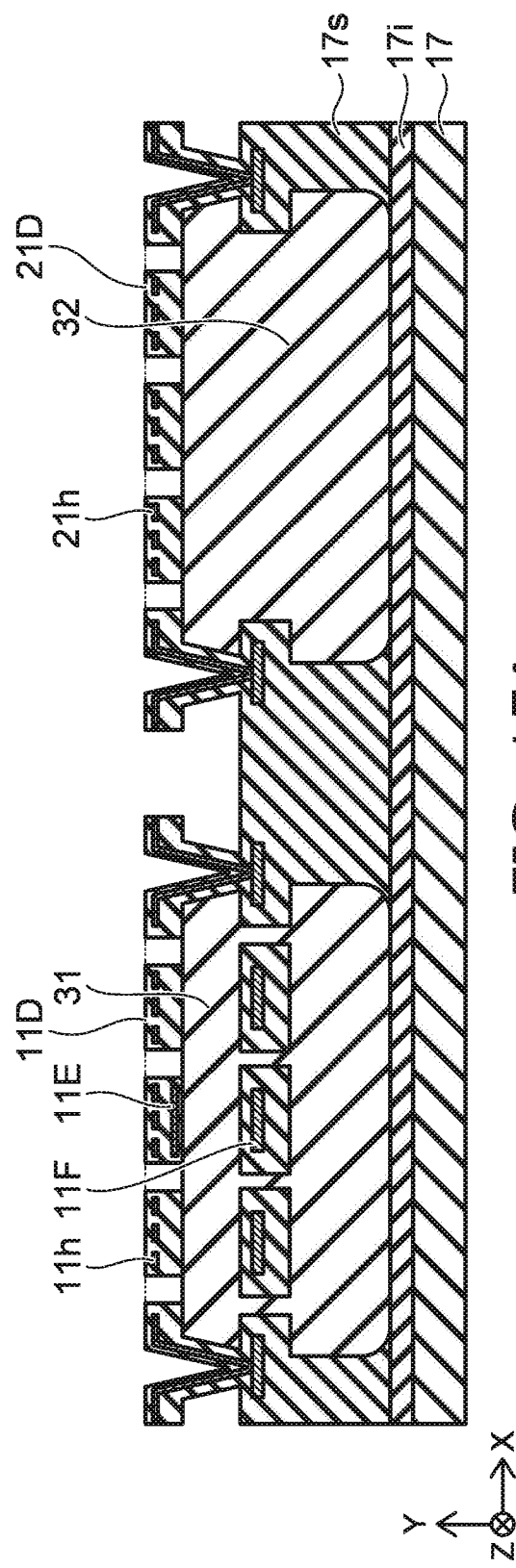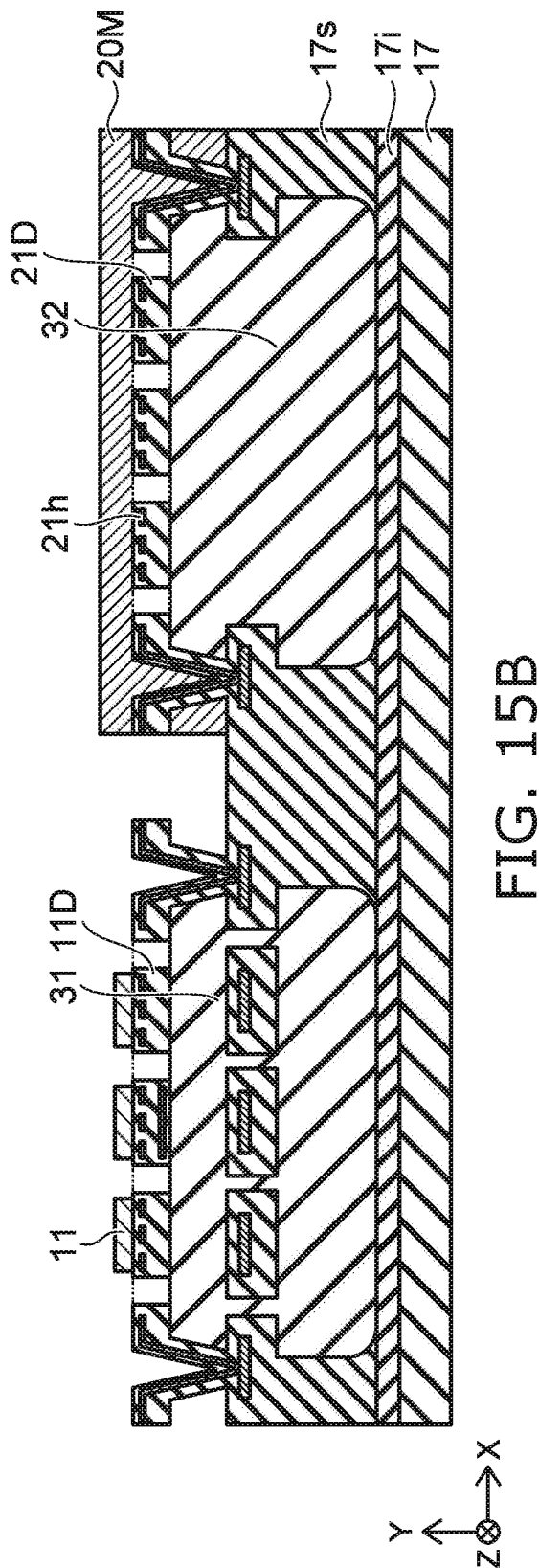

SENSOR AND METHOD FOR CALIBRATING SENSOR

CROSS-REFERENCE TO RELATED APPLICATIONS

This application is based upon and claims the benefit of priority from Japanese Patent Application No. 2019-185736, filed on Oct. 9, 2019; the entire contents of which are incorporated herein by reference.

FIELD

Embodiments of the invention generally relate to a sensor and a method for calibrating a sensor.

BACKGROUND

For example, it is desirable to obtain stable detection accuracy in a sensor.

BRIEF DESCRIPTION OF THE DRAWINGS

FIG. 15A and FIG. 15B are schematic cross-sectional views illustrating a method for manufacturing the sensor according to the third embodiment.

DETAILED DESCRIPTION

Figure 1:
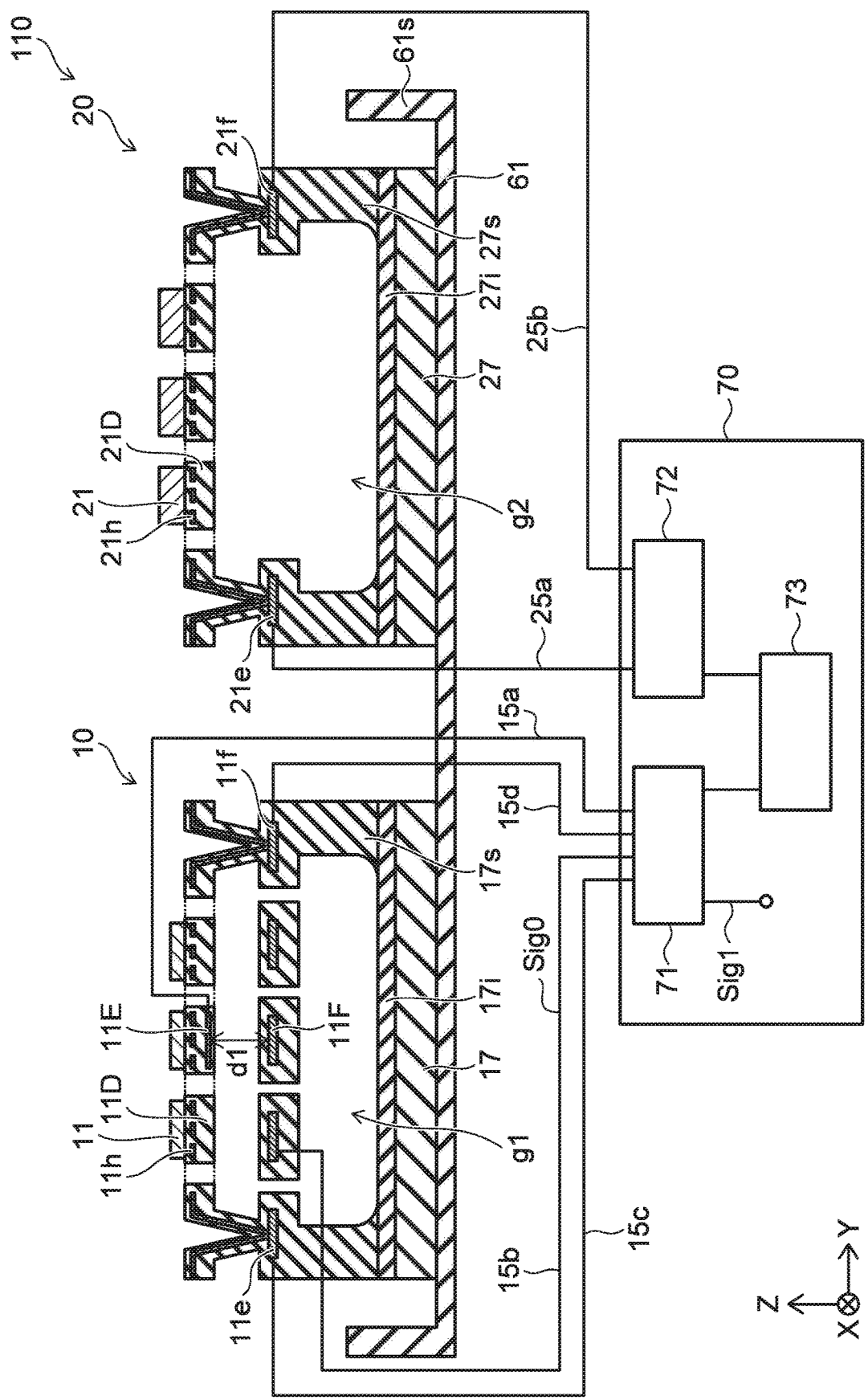
FIG. 1 is a schematic cross-sectional view illustrating a sensor according to a first embodiment.

According to one embodiment, a sensor includes a sensor part including a first film, and a structure body including a second film. The first film has a first density, and a first concentration of a first element. The second film has at least one of a second density, or a second concentration of the first element. The second concentration is greater than the first concentration. The second density is greater than the first density.

According to one embodiment, a method for calibrating a sensor is disclosed. The sensor includes a sensor part including a first film, and a structure body including a second film. The first film has a first density, and a first concentration of a first element. The second film has at least one of a second density, or a second concentration of the first element. The second concentration is greater than the first concentration. The second density is greater than the first density. The method can include causing the first element to be released from the second film of the sensor, and calibrating an output obtained from the sensor part when the first element is released.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

FIG. 1 is a schematic cross-sectional view illustrating a sensor according to a first embodiment.

As shown in FIG. 1, the sensor 110 according to the embodiment includes a sensor part 10 and a structure body 20. The sensor part 10 includes a first film 11. The structure body includes a second film 21.

The first film 11 has a first density, and a first concentration of a first element. The first element is an element to be detected. The first element is, for example, hydrogen. For example, the sensor 110 is a gas sensor detecting a gas including the first element.

As shown in FIG. 1, a controller 70 may be provided. The controller 70 includes, for example, a detection circuit 71. The detection circuit 71 is configured to output a detection signal Sig1. The detection signal Sig1 changes according to the concentration of the first element included in the gas at the periphery of the sensor part 10. Examples of the detection operation of the sensor part 10 are described below.

The second film 21 includes at least one of a second density, or a second concentration of the first element, such that the second concentration is greater than the first concentration, and the second density is greater than the first density. The second film 21 includes the first element (e.g., hydrogen). The first element is releasable from the second film 21.

For example, the first element can be released from the second film 21, and a gas including the first element can be detected by the sensor part 10. The characteristics of the sensor part 10 can be calibrated thereby. The structure body 20 that includes the second film 21 can be used for calibration. In the embodiment, the calibration can be easily performed. According to the embodiment, a sensor can be provided in which stable detection accuracy can be easily obtained.

As shown in FIG. 1, for example, the structure body 20 may include a heater 21h. The temperature of the second film 21 can be increased by using the heater 21h. Thereby, the first element can be efficiently released from the second film 21.

The controller 70 may include a heater circuit 72. The heater circuit 72 is electrically connected to the heater 21h. For example, the structure body 20 includes an electrode 21e and an electrode 21f. The electrode 21e is electrically connected to a portion of the heater 21h. The electrode 21f is electrically connected to another portion of the heater 21h. For example, the heater circuit 72 is electrically connected to the electrode 21e by wiring 25a. For example, the heater circuit 72 is electrically connected to the electrode 21f by wiring 25b.

The heater circuit 72 is configured to supply a current to the heater 21h. The second film 21 releases the first element (e.g., hydrogen, etc.) when the current is supplied to the heater 21h. For example, when performing the calibration, the current is supplied to the heater 21h by the heater circuit 72, and the temperature of the second film 21 increases. A gas that includes the first element (e.g., hydrogen) is released in a short period of time from the second film 21, and the gas is detected by the sensor part 10. The calibration is performed based on the detection result.

For example, the first film 11 can store the first element (e.g., hydrogen, etc.). The characteristics of the first film 11 change when the first film 11 stores the first element. For example, when the first film 11 stores the first element, the first film 11 expands, and the volume of the first film 11 increases. The characteristics (e.g., the volume, etc.) of the first film are changeable according to the change of the concentration of the first element included in the gas at the periphery of the first film 11. By detecting a signal corresponding to the change of the characteristics of the first film 11, the existence or absence of the first element or the concentration of the first element at the periphery of the first film 11 can be detected.

In the example, the sensor part 10 includes a first electrode 11E and a second electrode 11F. For example, the first film 11 is fixed to the first electrode 11E. An electrical signal that is generated between the first electrode 11E and the second electrode 11F changes according to the change of the characteristics (e.g., the volume) of the first film 11. By detecting the change of the electrical signal, the existence or absence of the first element or the concentration of the first element at the periphery of the first film 11 can be detected.

For example, a film portion 11D (e.g., a diaphragm) in which the first film 11 is provided deforms when the first film 11 expands. The deformation of the film portion 11D is caused by stress generated by the expansion of the first film 11. A distance d1 between the first electrode 11E and the second electrode 11F changes when the film portion 11D deforms. The electrostatic capacitance between the first electrode 11E and the second electrode 11F changes when the distance between the first electrode 11E and the second electrode 11F changes. By detecting the change of the electrostatic capacitance, the existence or absence of the first element or the concentration of the first element at the periphery of the first film 11 can be detected. In the example, the sensor part 10 has a MEMS (Micro Electro Mechanical Systems) structure.

As described above, for example, the controller 70 includes the detection circuit 71. The detection circuit 71 is electrically connected to the first and second electrodes 11E and 11F. For example, the detection circuit 71 is electrically connected to the first electrode 11E by wiring 15a. For example, the detection circuit 71 is electrically connected to the second electrode 11F by wiring 15b. The detection circuit 71 is configured to output the detection signal Sig1. The detection signal Sig1 changes according to the concentration of the first element (e.g., hydrogen) included in the gas at the periphery of the sensor part 10.

Thus, in one example, the distance d1 between the first electrode 11E and the second electrode 11F changes according to the concentration of the first element included in the gas at the periphery of the sensor part 10. The first element can be detected by detecting the change of the distance d1 as the change of the electrostatic capacitance. In the embodiment, other characteristics (e.g., the conductivity, etc.) of the first film 11 may change according to the concentration of the first element included in the gas at the periphery of the sensor part 10. The first element can be detected by detecting the change of the other characteristic.

For example, a sensor signal Sig0 is outputtable from the sensor part 10. The sensor signal Sig0 is generated between the first electrode 11E and the second electrode 11F. For example, the sensor signal Sig0 is generated between the wiring 15a and the wiring 15b. The sensor signal Sig0 changes according to the concentration of the first element included in the gas at the periphery of the sensor part 10. For example, the detection signal Sig1 that is output from the detection circuit 71 corresponds to the sensor signal Sig0. The detection circuit 71 can process the sensor signal Sig0 and output the processed sensor signal Sig0 as the detection signal Sig1. The processing may include, for example, amplification. The amplification may include deriving a difference between a reference value.

As shown in FIG. 1, the controller 70 may include a control circuit 73. For example, when the first element is released from the second film 21, the control circuit 73 may cause the detection signal Sig1 to be output from the detection circuit 71 by calibrating a signal (e.g., the sensor signal Sig0) obtained from the first and second electrodes 11E and 11F. The control circuit 73 may include, for example, a CPU (Central Processing Unit), etc. At least one of the detection circuit 71 or the heater circuit 72 may be controlled by the control circuit 73. At least a portion of the controller 70 may be included in the sensor 110. At least a portion of the controller 70 may be provided separately from the sensor 110.

In the example, the film portion 11D of the sensor part 10 includes a heater 11h. For example, the first element that is stored in the first film 11 can be released from the first film 11 by the heater 11h increasing the temperature of the first film 11. For example, a portion of the heater 11h is electrically connected to an electrode 11e. The electrode 11e is electrically connected to the detection circuit 71 by wiring 15c. For example, another portion of the heater 11h is electrically connected to an electrode 11f. The electrode 11f is electrically connected to the detection circuit 71 by wiring 15d.

In the example, the sensor part 10 includes a substrate 17, an insulating film 17i, and a supporter 17s. The insulating film 17i is provided on the substrate 17, and the supporter 17s is provided on the insulating film 17i. The second electrode 11F is supported by the supporter 17s. For example, a gap g1 may be provided between the second electrode 11F and the substrate 17 (and the insulating film 17i). Insulating portions may be provided at the upper and lower surfaces of the second electrode 11F.

The supporter 17s supports the film portion 11D. Thereby, a gap can be formed between the film portion 11D and the portion including the second electrode 11F. The distance d1 between the second electrode 11F and the first electrode 11E included in the film portion 11D is changeable thereby.

The direction from the second electrode 11F toward the first electrode 11E is taken as a Z-axis direction. One direction perpendicular to the Z-axis direction is taken as an X-axis direction. A direction perpendicular to the Z-axis direction and the X-axis direction is taken as a Y-axis direction.

The distance d1 between the first electrode 11E and the second electrode 11F is the length along the Z-axis direction. The film portion 11D is along the X-Y plane. For example, the first electrode 11E that is included in the film portion 11D is displaced in the Z-axis direction due to the change of the characteristics of the first film 11 according to the concentration of the first element at the periphery of the sensor part 10.

In the example, the insulating film 17i is provided between the substrate 17 and the first film 11 in the Z-axis direction. The second electrode 11F is provided between the insulating film 17i and the first film 11 in the Z-axis direction. The first electrode 11E is provided between the second electrode 11F and the first film 11 in the Z-axis direction. The heater 11h is provided between the first electrode 11E and the first film 11 in the Z-axis direction.

For example, the first film 11 is exposed. The first film 11 can efficiently contact the gas including the first element. The temperature of the first film 11 can be efficiently increased by the heater 11h. Thereby, the first element that is stored in the first film 11 can be efficiently released from the first film 11.

In the example, the structure body 20 includes a substrate 27, an insulating film 27i, and a supporter 27s. The insulating film 27i is provided on the substrate 27, and the supporter 27s is provided on the insulating film 27i. The second film 21 and a structure portion 21D including the heater 21h are supported by the supporter 27s.

In the example, a gap g2 is provided between the substrate 27 (and the insulating film 27i) and the structure portion 21D including the heater 21h. The transfer of the heat from the heater 21h toward the substrate 27 side can be suppressed. The temperature of the second film 21 can be efficiently increased by the heater 21h.

The configuration of the structure body 20 may be similar to the configuration of the sensor part 10. The sensor part 10 and the structure body 20 can be efficiently manufactured thereby.

For example, the first film 11 includes a second element. The second element includes at least one selected from the group consisting of Pd, Pt, and Au. When the first element is hydrogen, the second element may function as a catalyst.

The first film 11 may include a third element in addition to the second element. The third element includes at least one selected from the group consisting of Si, P, and B. When the first element is hydrogen, for example, a high reaction rate is obtained by the first film 11 including the third element.

The first film 11 may further include a fourth element in addition to the second and third elements. The fourth element includes at least one selected from the group consisting of Cu, Ag, Ni, Fe, and Cr. When the first element is hydrogen, for example, a high reaction rate is obtained by the first film 11 including the fourth element.

In the embodiment, for example, the first film 11 is amorphous, and the second film 21 includes a crystal. Or, the second film 21 has a higher crystallinity than the crystallinity of the first film 11. By setting the first film 11 to be amorphous, the first film 11 can efficiently store the first element. By setting the crystallinity of the first film 11 to be low, the first film 11 can efficiently store the first element.

The composition of the material included in the second film 21 may be similar to the composition of the material included in the first film 11. The characteristics of the second film 21 can be modified from the characteristics of the first film 11 by modifying the conditions of the formation processes of the second film 21 from the conditions of the formation processes of the first film 11. The difference between the characteristics of the first film 11 and the characteristics of the second film 21 includes, for example, at least one of a difference between densities or a difference between concentrations of the first element. The difference between the characteristics of the first film 11 and the characteristics of the second film 21 may include, for example, a difference of crystallinities.

In the example as shown in FIG. 1, the sensor 110 includes a first member 61. The sensor part 10 is provided at one region of the first member 61. The structure body 20 is provided at another region of the first member 61. The direction from the sensor part 10 toward the structure body 20 is along a direction crossing a first direction (e.g., the Z-axis direction).

The first member 61 may include a first side portion 61s. For example, the sensor part 10 and the structure body 20 are between two portions of the first side portion 61s. The first member 61 is, for example, at least a portion of a package.

Figure 2A:
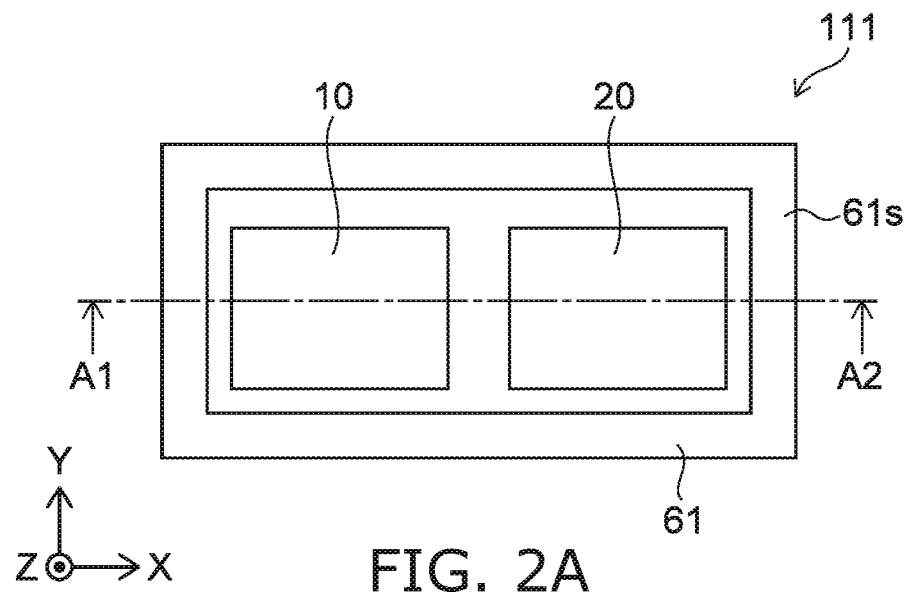
FIG. 2A and FIG. 2B are schematic views illustrating a sensor according to the first embodiment.
Figure 2B:
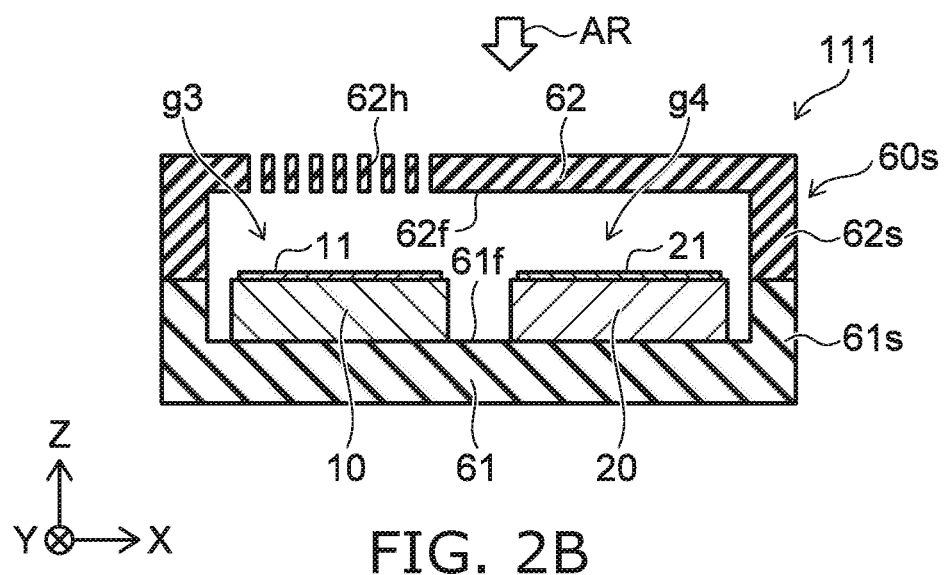

FIG. 2A and FIG. 2B are schematic views illustrating a sensor according to the first embodiment.

FIG. 2A is a see-through plan view as viewed along arrow AR of FIG. 2B. FIG. 2B is a line A1-A2 cross-sectional view of FIG. 2A.

As shown in FIG. 2B, the sensor 111 according to the embodiment includes the first member 61 and a second member 62 in addition to the sensor part 10 and the structure body 20. The configurations described in reference to the sensor 110 are applicable to the configurations of the sensor part 10 and the structure body 20. An example of the first and second members 61 and 62 will now be described. For example, a package is formed of the first and second members 61 and 62.

The second member 62 includes a hole 62h. The sensor part 10 and the structure body 20 are provided between the first member 61 and the second member 62. For example, the distance between the hole 62h and the sensor part 10 is less than the distance between the hole 62h and the structure body 20. For example, the sensor part 10 is provided at a position proximate to the hole 62h. The structure body 20 is provided at a position far from the hole 62h.

For example, the gas that includes the first element (e.g., hydrogen) reaches the sensor part 10 via the hole 62h. The gas that includes the first element is the gas to be detected. The first element that is included in the gas contacts the first film 11 of the sensor part 10. The first element is detected by the sensor part 10 in the detection operation of the sensor 111.

In the calibration operation of the sensor 111, the first element is released from the second film 21 of the structure body 20. The first element that is released reaches the first film 11 and is detected by the sensor part 10. Because the distance between the second film 21 and the hole 62h is long as described above, the first element that is released from the second film 21 easily contacts the first film 11. The first element that is released from the second film 21 is suppressed from outflowing through the hole 62h without being able to reach the first film 11. The calibration can be efficiently performed by setting the distance between the hole 62h and the sensor part 10 to be less than the distance between the hole 62h and the structure body 20.

As shown in FIG. 2B, the first member 61 includes a first surface 61f. The second member 62 includes a second surface 62f. The first surface 61f faces the second member 62. The second surface 62f faces the first member 61. The first surface 61f and the second surface 62f face each other. In the sensor 111, the sensor part 10 and the structure body 20 are provided at the first surface 61f.

In the example, the direction from the sensor part 10 toward the hole 62h is along the Z-axis direction. The direction from the sensor part 10 toward the structure body 20 crosses the Z-axis direction. The hole 62h overlaps the sensor part 10 in the Z-axis direction. A gap g3 is provided between the sensor part 10 and the hole 62h.

A gap g4 is provided between the structure body 20 and the second member 62. In the calibration operation, the gas that includes the first element released from the second film 21 reaches the first film 11 via the gap g4.

As shown in FIG. 2A and FIG. 2B, the first member 61 may include the first side portion 61s. The second member 62 may include a second side portion 62s. For example, the first side portion 61s is linked to the second side portion 62s. For example, at least a portion of the sensor part 10 may be provided between one portion of the first side portion 61s and another portion of the first side portion 61s. For example, at least a portion of the structure body 20 may be provided between one portion of the first side portion 61s and another portion of the first side portion 61s. For example, at least a portion of the sensor part 10 may be provided between one portion of the second side portion 62s and another portion of the second side portion 62s. For example, at least a portion of the structure body 20 may be provided between one portion of the second side portion 62s and another portion of the second side portion 62s.

For example, at least one of the first member 61 or the second member 62 may include a side portion 60s (referring to FIG. 2B). For example, the side portion 60s includes at least one of the first side portion 61s or the second side portion 62s. At least a portion of the structure body 20 is between the sensor part 10 and the side portion 60s. For example, the structure body 20 is depthward in the space formed by the first member 61 and the second member 62. Thereby, the gas that includes the first element released from the second film 21 of the structure body 20 is suppressed from outflowing to the outside, and the gas that includes the first element is efficiently supplied to the first film 11.

Figure 3:
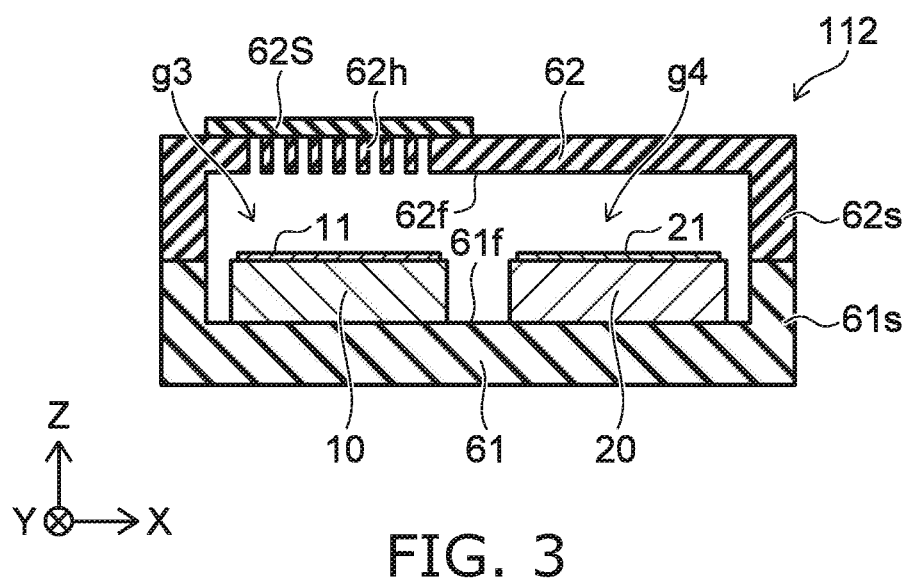
FIG. 3 is a schematic cross-sectional view illustrating a sensor according to the first embodiment.

FIG. 3 is a schematic cross-sectional view illustrating a sensor according to the first embodiment.

In the sensor 112 as shown in FIG. 3, the second member 62 includes a shutter 62S. For example, in a first state, the shutter 62S blocks at least a portion of the hole 62h. In the calibration operation, at least a portion of the hole 62h is blocked by the shutter 62S. Thereby, in the calibration operation, the gas that includes the first element released from the second film 21 can be suppressed from outflowing to the outside.

In the detection operation of the sensor 112, the shutter 62S may include a second state. The surface area of the hole 62h blocked by the shutter 62S in the second state is less than the surface area of the hole 62h blocked by the shutter 62S in the first state. Thereby, in the detection operation, the gas from the outside efficiently reaches the first film 11 via the hole 62h.

Figure 4A:
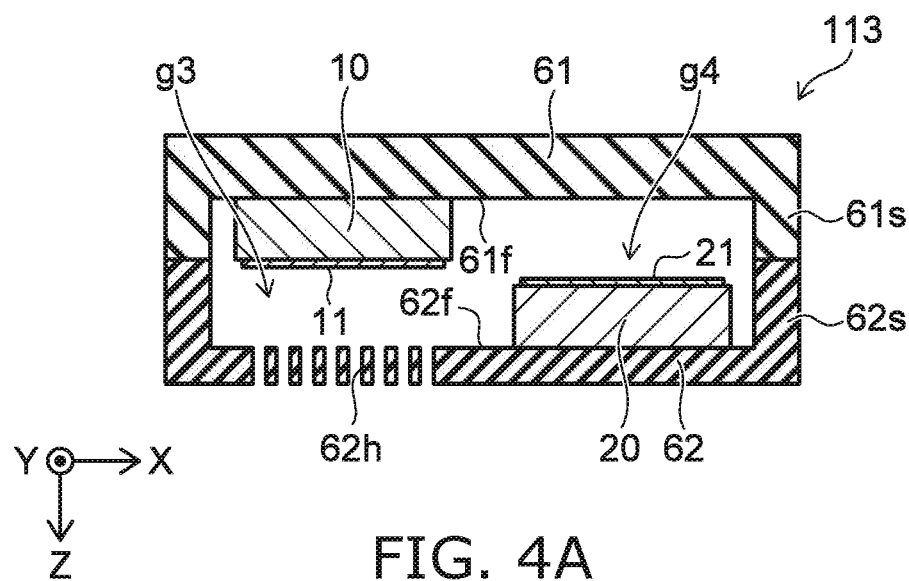
FIG. 4A and FIG. 4B are schematic cross-sectional views illustrating sensors according to the first embodiment.
Figure 4B:
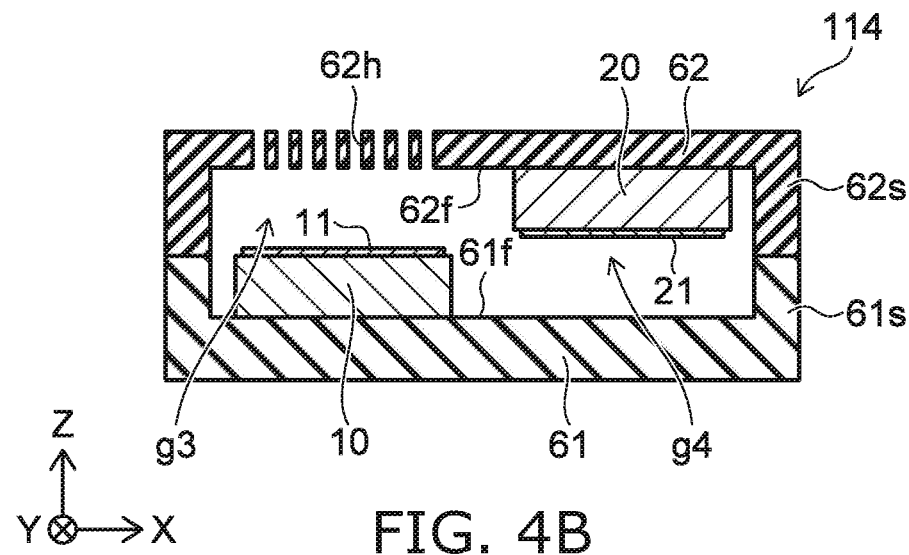

FIG. 4A and FIG. 4B are schematic cross-sectional views illustrating sensors according to the first embodiment.

As shown in FIG. 4A, the sensor part 10, the structure body 20, the first member 61, and the second member 62 are provided in a sensor 113 according to the embodiment as well. The first member 61 includes the first surface 61f. The second member 62 includes the second surface 62f. The second surface 62f faces the first surface 61f. The second member 62 includes the hole 62h. The structure body 20 is provided at the second surface 62f. The sensor part 10 is provided at the first surface 61f.

In the sensor 113, the sensor part 10 overlaps the hole 62h in the direction (the direction along the Z-axis direction) from the first member 61 toward the second member 62. The structure body 20 does not overlap the hole 62h in the direction recited above (the direction along the Z-axis direction).

In the sensor 113, for example, the sensor part 10 is above the hole 62h. For example, when the gas that includes the first element is lighter than air, the gas that includes the first element efficiently reaches the first film 11 by passing through the hole 62h. For example, the gas that includes the first element is suppressed from reaching the second film 21.

As shown in FIG. 4B, the sensor part 10, the structure body 20, the first member 61, and the second member 62 are provided in a sensor 114 according to the embodiment as well. The structure body 20 is provided at the second surface 62f. The sensor part 10 is provided at the first surface 61f. The sensor part 10 overlaps the hole 62h in the direction (the direction along the Z-axis direction) from the first member 61 toward the second member 62. The structure body 20 does not overlap the hole 62h in the direction recited above (the direction along the Z-axis direction).

In the sensor 114, for example, the hole 62h is above the sensor part 10. For example, when the gas that includes the first element is heavier than air, the gas that includes the first element efficiently reaches the first film 11 by passing through the hole 62h. For example, the gas that includes the first element is suppressed from reaching the second film 21.

Figure 5A:
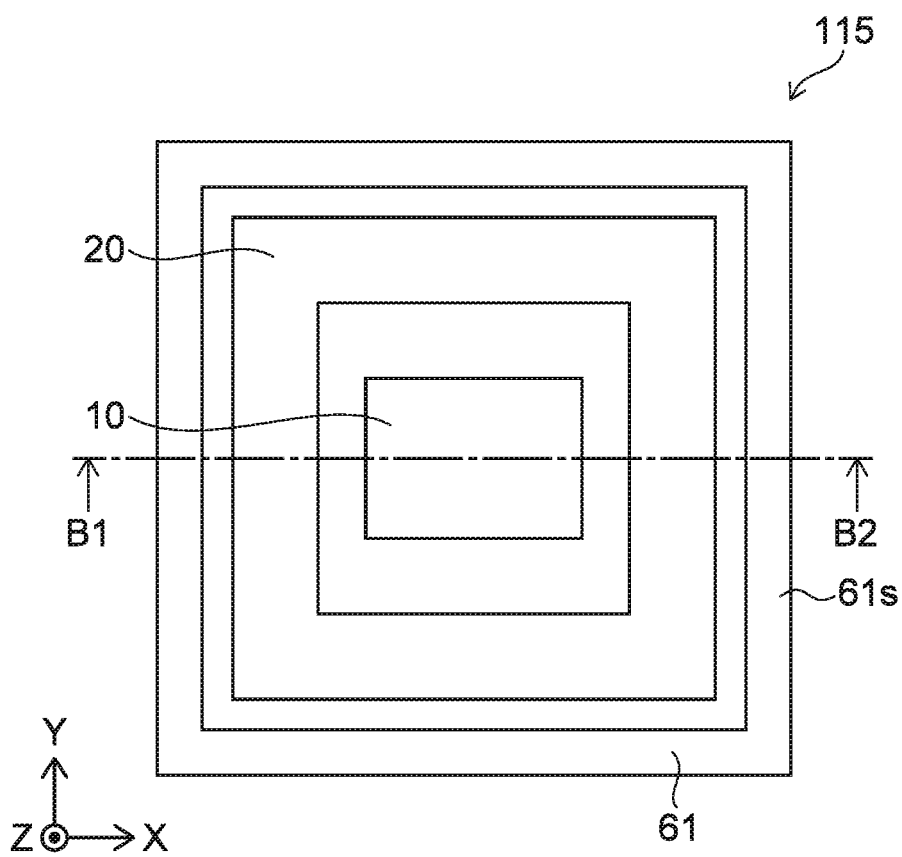
FIG. 5A and FIG. 5B are schematic views illustrating a sensor according to the first embodiment.
Figure 5B:
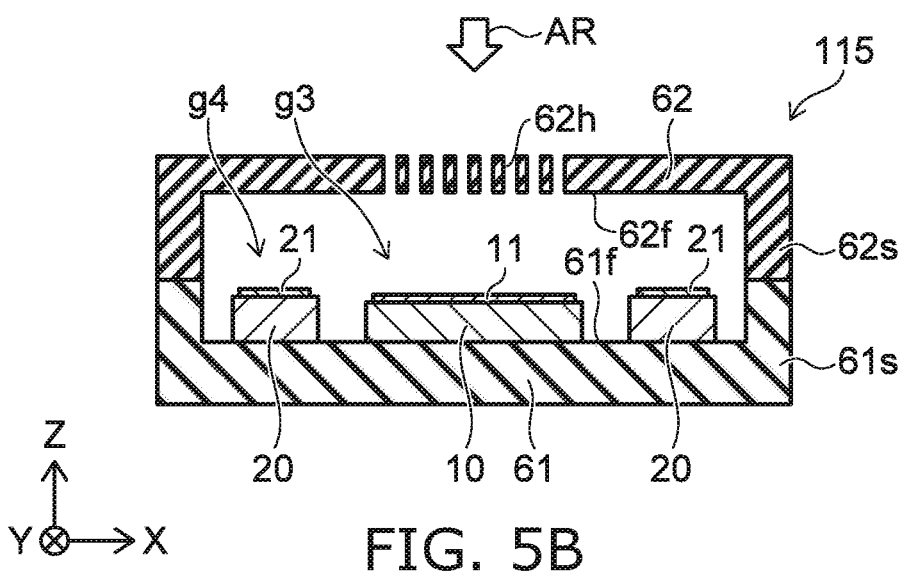

FIG. 5A and FIG. 5B are schematic views illustrating a sensor according to the first embodiment.

FIG. 5A is a see-through plan view as viewed along arrow AR of FIG. 5B. FIG. 5B is a line B1-B2 cross-sectional view of FIG. 5A.

As shown in FIG. 5B, the sensor 115 according to the embodiment includes the sensor part 10, the structure body 20, the first member 61, and the second member 62. In the example, the sensor part 10 and the structure body 20 are provided at the first surface 61f of the first member 61. The second member 62 includes the hole 62h. The hole 62h overlaps the sensor part 10 in the direction (the direction along the Z-axis direction) from the first member 61 toward the second member 62.

In the sensor 115, at least a portion of the sensor part 10 is between a portion of the structure body 20 and another portion of the structure body 20. The gas that includes the first element is efficiently supplied to the first film 11 from the second film 21 included in the portion of the structure body 20 and the second film 21 included in the other portion of the structure body 20. An efficient calibration can be performed. For example, the structure body 20 is provided around the sensor part 10 in the X-Y plane. For example, the sensor part 10 may be surrounded with the structure body 20 in the X-Y plane.

Figure 6:
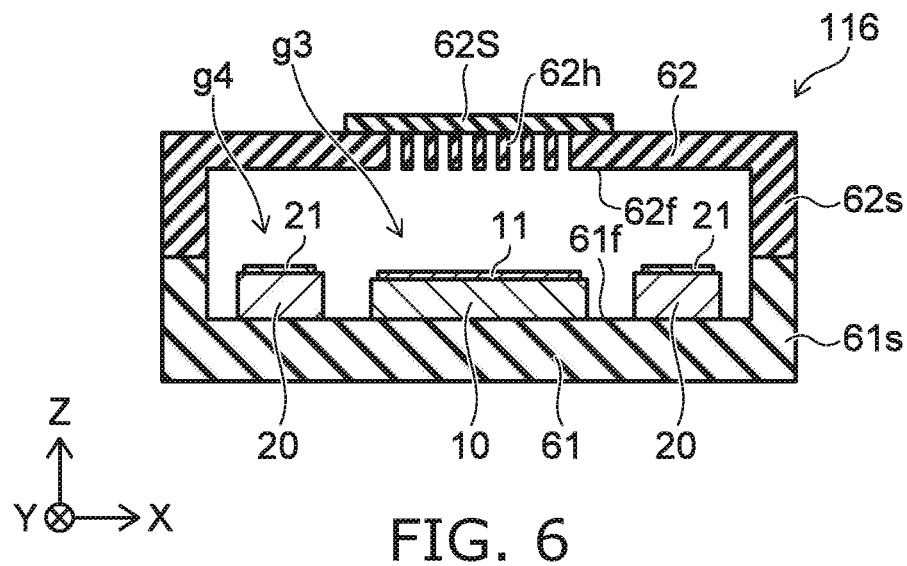
FIG. 6 is a schematic cross-sectional view illustrating a sensor according to the first embodiment.

FIG. 6 is a schematic cross-sectional view illustrating a sensor according to the first embodiment.

In the sensor 116 as shown in FIG. 6, the second member 62 includes the shutter 62S. In the first state, the shutter 62S blocks at least a portion of the hole 62h. In the calibration operation, the gas that includes the first element released from the second film 21 can be suppressed from outflowing to the outside. In the detection operation, the shutter 62S may include the second state. The surface area of the hole 62*h* blocked by the shutter 62S in the second state is less than the surface area of the hole 62*h* blocked by the shutter 62S in the first state. Thereby, for example, in the detection operation, the gas from the outside efficiently reaches the first film 11 via the hole 62*h*.

Figure 7:
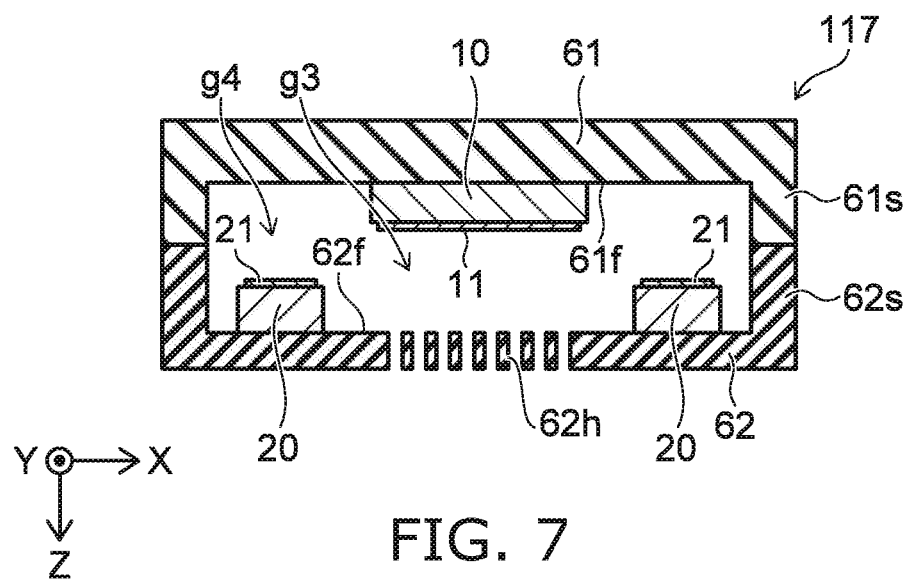
FIG. 7 is a schematic cross-sectional view illustrating a sensor according to the first embodiment.

FIG. 7 is a schematic cross-sectional view illustrating a sensor according to the first embodiment.

As shown in FIG. 7, the sensor part 10, the structure body 20, the first member 61, and the second member 62 are provided in the sensor 117 according to the embodiment as well. The first member 61 includes the first surface 61*f*. The second member 62 includes the second surface 62*f*. The second surface 62*f* faces the first surface 61*f*. The second member 62 includes the hole 62*h*. The structure body 20 is provided at the second surface 62*f*. The sensor part 10 is provided at the first surface 61*f*. In the sensor 117, the sensor part 10 overlaps the hole 62*h* in the direction (the direction along the Z-axis direction) from the first member 61 toward the second member 62. The structure body 20 does not overlap the hole 62*h* in the direction recited above (the direction along the Z-axis direction). An efficient calibration can be performed.

Figure 8:
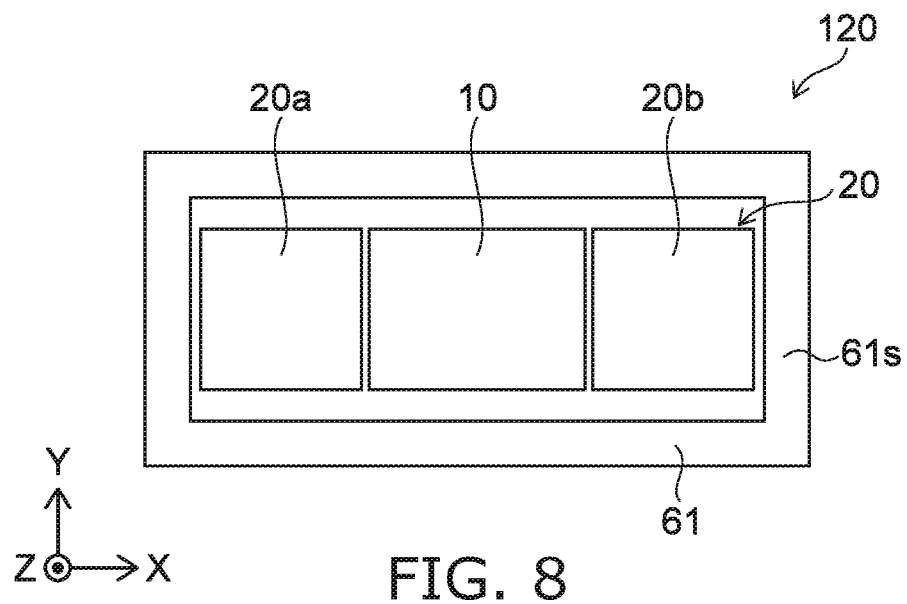
FIG. 8 is a schematic plan view illustrating a sensor according to the first embodiment.

FIG. 8 is a schematic plan view illustrating a sensor according to the first embodiment.

As shown in FIG. 8, the sensor 120 includes the sensor part 10 and the structure body 20. The sensor 120 includes multiple structure bodies 20. The multiple structure bodies 20 include a first structure body 20*a* and a second structure body 20*b*. At least a portion of the sensor part 10 is between the first structure body 20*a* and the second structure body 20*b*. For example, the direction from the first structure body 20*a* toward the second structure body 20*b* is along the X-axis direction. An efficient calibration can be performed.

Figure 9:
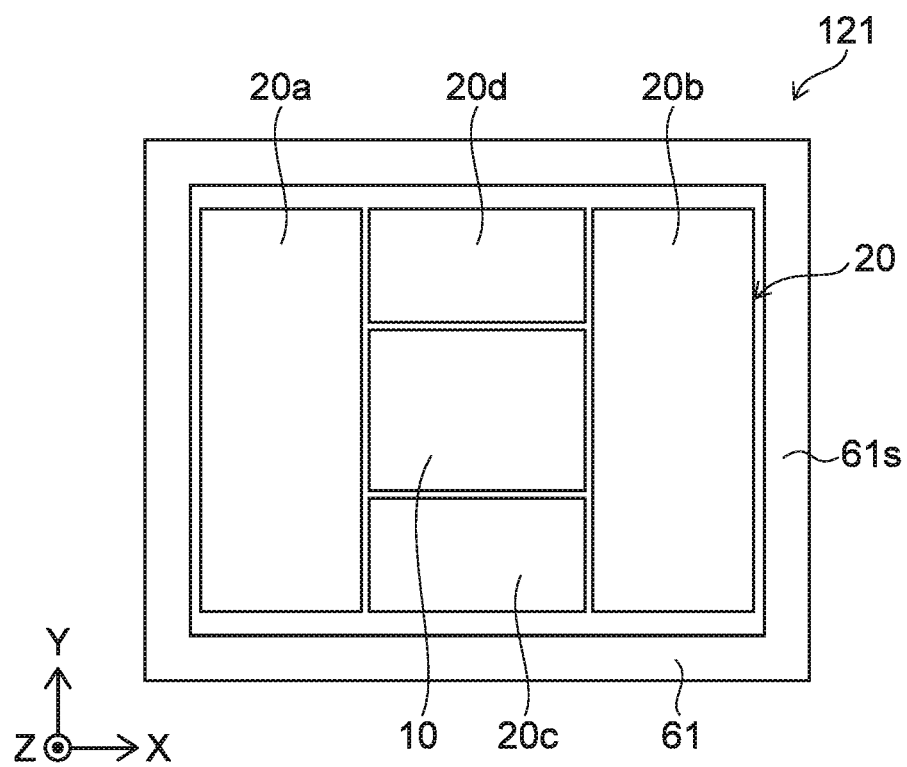
FIG. 9 is a schematic plan view illustrating a sensor according to the first embodiment.

FIG. 9 is a schematic plan view illustrating a sensor according to the first embodiment.

As shown in FIG. 9, the sensor 121 includes the sensor part 10 and the multiple structure bodies 20. The multiple structure bodies 20 include a third structure body 20*c* and a fourth structure body 20*d* in addition to the first structure body 20*a* and the second structure body 20*b*. At least a portion of the sensor part 10 is between the first structure body 20*a* and the second structure body 20*b* in the X-axis direction. At least a portion of the sensor part 10 is between the third structure body 20*c* and the fourth structure body 20*d* in a direction (e.g., the Y-axis direction) crossing the direction (the X-axis direction) from the first structure body 20*a* toward the second structure body 20*b*. An efficient calibration can be performed.

In the sensor 120 and the sensor 121, the release of the gas including the first element from the second film 21 included in the second structure body 20*b* and the release of the gas including the first element from the second film 21 included in the first structure body 20*a* may be simultaneously performed. The release of the gas including the first element from the second film 21 included in the second structure body 20*b* may be performed separately from the release of the gas including the first element from the second film 21 included in the first structure body 20*a*. The operations of the multiple structure bodies 20 may be performed independently of each other.

Figure 10A:
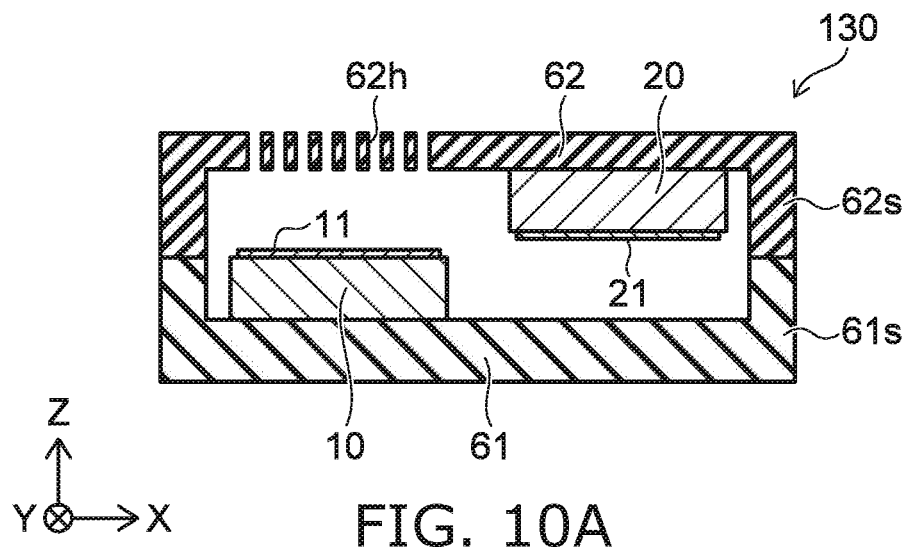
FIG. 10A and FIG. 10B are schematic cross-sectional views illustrating a sensor according to the first embodiment.
Figure 10B:
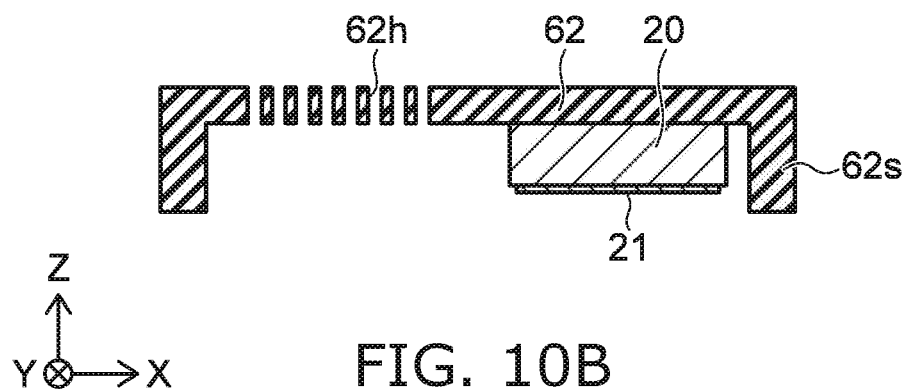

FIG. 10A and FIG. 10B are schematic cross-sectional views illustrating a sensor according to the first embodiment.

As shown in FIG. 10A, the sensor part 10, the structure body 20, the first member 61, and the second member 62 are provided in the sensor 130. In the example, the structure body 20 is fixed to the second member 62. The sensor 130 includes a state in which the first member 61 and the second member 62 are linked to each other (the state of FIG. 10A).

As shown in FIG. 10B, the sensor 130 may include a state in which the second member 62 is separated from the first member 61.

The detection operation and the calibration operation are performed in the state in which the first member 61 and the second member 62 are linked to each other. After the calibration operation has ended, the second member 62 on which the structure body 20 is provided may be replaced with another second member 62. The calibration can be easily performed in the sensor 130. A sensor can be provided in which stable detection accuracy can be easily obtained.

Figure 11:
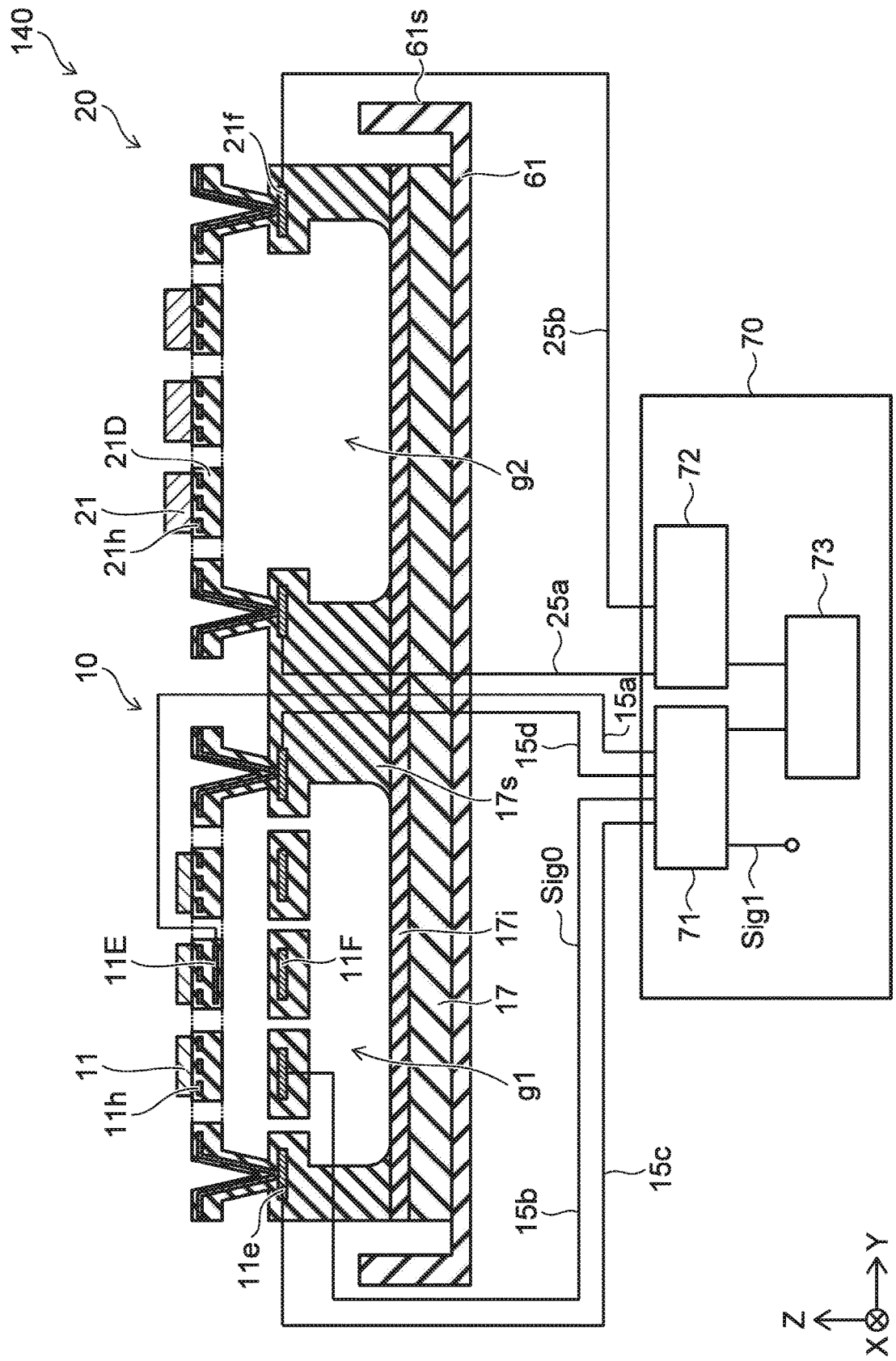
FIG. 11 is a schematic cross-sectional view illustrating a sensor according to the first embodiment.

FIG. 11 is a schematic cross-sectional view illustrating a sensor according to the first embodiment.

As shown in FIG. 11, the sensor part 10, the structure body 20, and the first member 61 are provided in the sensor 140. The second member 62 may be provided. In the example, the sensor part 10 is provided at one region of one substrate 17, and the structure body 20 is provided at another region of the one substrate 17. The calibration can be easily performed in the sensor 140. A sensor can be provided in which stable detection accuracy can be easily obtained.

Second Embodiment

A second embodiment relates to a method for calibrating a sensor.

Figure 12:
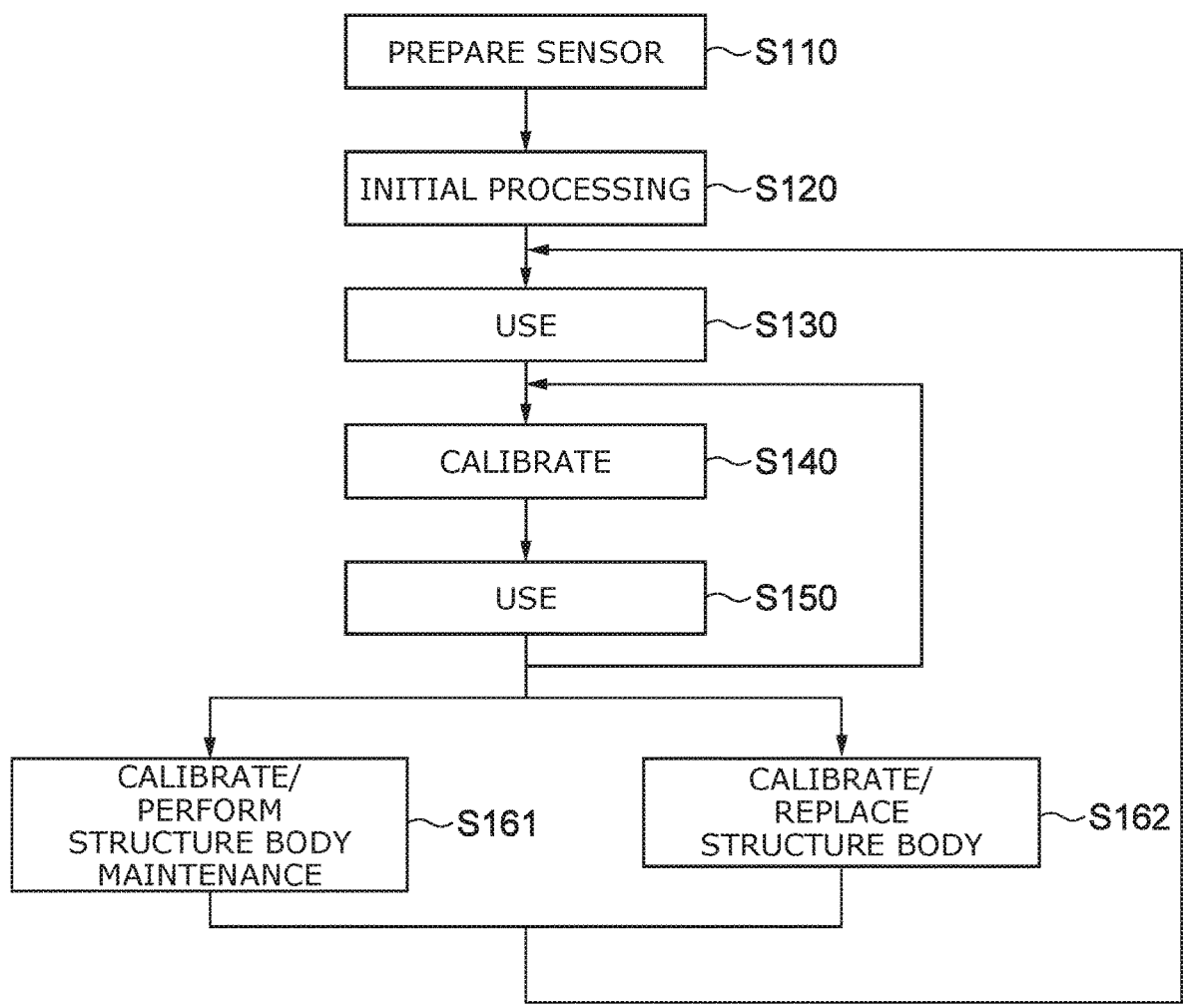
FIG. 12 is a flowchart illustrating the method for calibrating the sensor according to the second embodiment.

FIG. 12 is a flowchart illustrating the method for calibrating the sensor according to the second embodiment. As shown in FIG. 12, a sensor is prepared (step S110). The sensor may be any sensor according to the first embodiment. The sensor includes the sensor part 10 including the first film 11, and the structure body 20 including the second film 21.

In the embodiment, an initial processing of introducing the first element to the second film 21 (step S120) may be performed. For example, the second film 21 is exposed to an atmosphere including the first element. For example, the second film 21 is caused to contact a gas including the first element. The time of exposing the second film 21 to the atmosphere including the first element is, for example, not less than 1 minute and not more than 10 days. The exposure time is arbitrary. When exposing the second film 21 to the atmosphere including the first element, at least one of the temperature of the second film 21 or the temperature of the atmosphere may be increased. By increasing the temperature, the first element is introduced to the second film 21 in a short period of time. When the temperature of the second film 21 is increased, the temperature of the second film 21 is reduced to, for example, room temperature (25° C.) or the like before removing the second film 21 from the atmosphere including the first element.

The sensor is used (step S130). For example, calibration is performed (step S140) when the usage time of the sensor has reached a determined period or when the output of the sensor is determined to be abnormal. In the calibration, the first element is released from the second film 21. For example, the temperature of the second film 21 is increased by the heater 21*h*. Thereby, the first element is released from the second film 21. The gas that includes the first element reaches the first film 11 of the sensor part 10. The calibration of the sensor part 10 is performed based on the signal obtained from the sensor part 10 in this state.

For example, the "zero point" of the value of the intensity of the signal obtained from the sensor part 10 or the like is corrected. For example, the amplification factor of the intensity of the signal obtained from the sensor part 10 or the like is corrected.

The sensor is used (step S150). After step S150, the flow may return to step S140. Step S140 and step S150 may be performed repeatedly. The first element may be released in order from the multiple structure bodies 20 (e.g., the first to fourth structure bodies 20a to 20d, etc.) by repeating step S140 and step S150. For example, such an operation may be controlled by the control circuit 73.

For example, the repetition of steps including step S140 and step S150 may be performed without the operation of a human. For example, these steps may be performed by the controller 70.

For example, the operation may be performed by an operator when the time of the operation including step S140 and step S150 has reached a determined time or when the output of the sensor is determined to be abnormal. For example, the calibration by the operator and the maintenance of the structure body 20 may be performed (step S161). For example, the calibration by the operator and the replacement of the structure body 20 may be performed (step S162). In the calibration by the operator, the gas that includes the first element is supplied to the first film 11 by the operator, and the calibration of the sensor part 10 is performed. The maintenance of the structure body 20 may include introducing the first element to the second film 21 included in the structure body 20, etc. After step S161 or step S162, the flow may return to step S130.

Thus, in the method for calibrating the sensor according to the embodiment, the sensor includes, for example, the sensor part 10 including the first film 11, and the structure body 20 including the second film 21. For example, the first film 11 has the first density and the first concentration of the first element. For example, the second film includes at least one of the second density that is greater than the first density, or the second concentration of the first element that is greater than the first concentration. In the calibration method according to the embodiment, the first element is released from the second film 21 of the sensor. For example, the first element is released from the second film 21 by the heater 21h increasing the temperature of the second film 21. In the method for calibrating the sensor according to the embodiment, the output that is obtained from the sensor part 10 when the first element is released is calibrated.

According to the second embodiment, a method for calibrating a sensor can be provided in which stable detection accuracy can be easily obtained.

Third Embodiment

A third embodiment relates to a method for manufacturing a sensor.

Figure 13A:
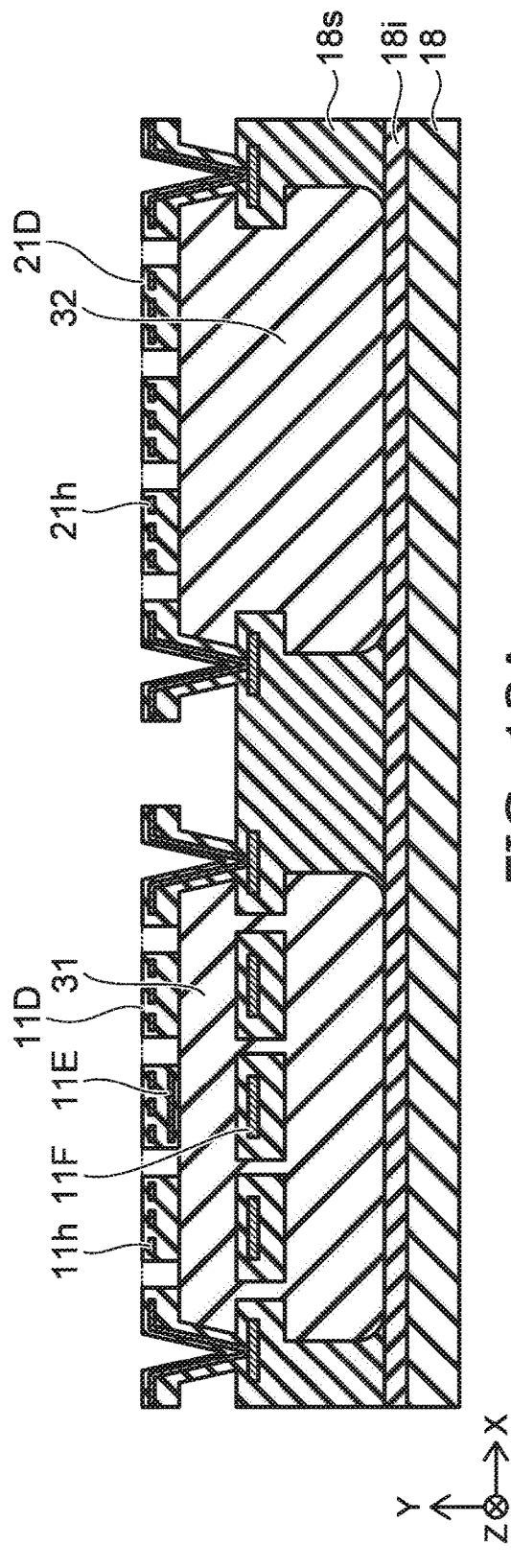
FIG. 13A and FIG. 13B are schematic cross-sectional views illustrating the method for manufacturing the sensor according to the third embodiment.
Figure 13B:
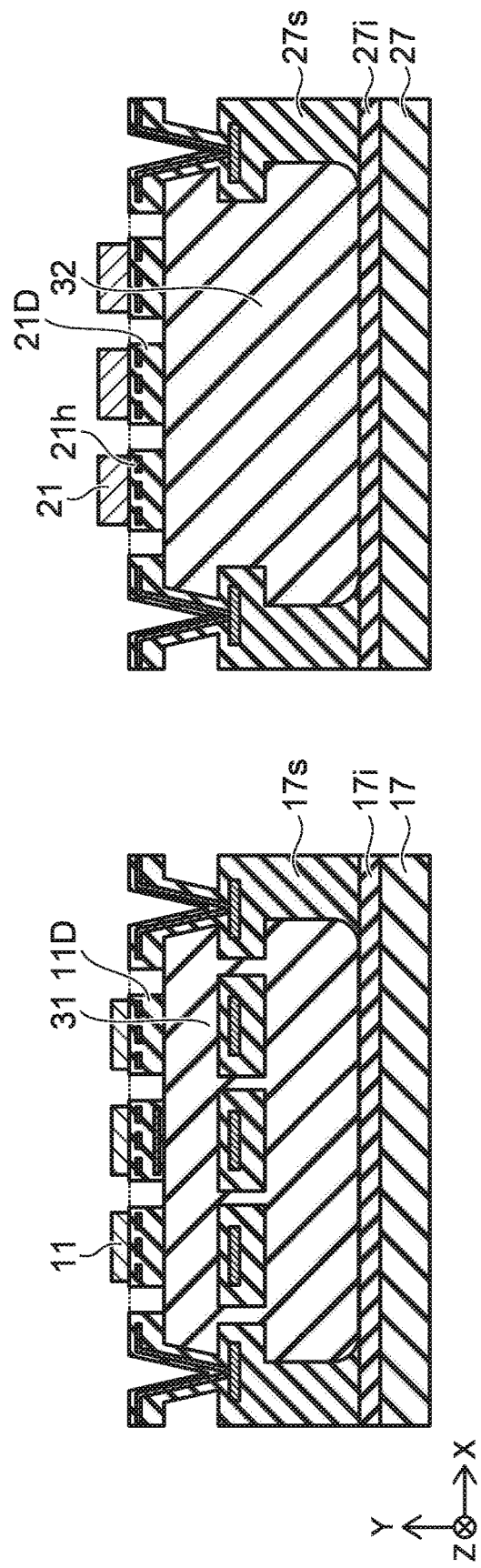
Figure 14:
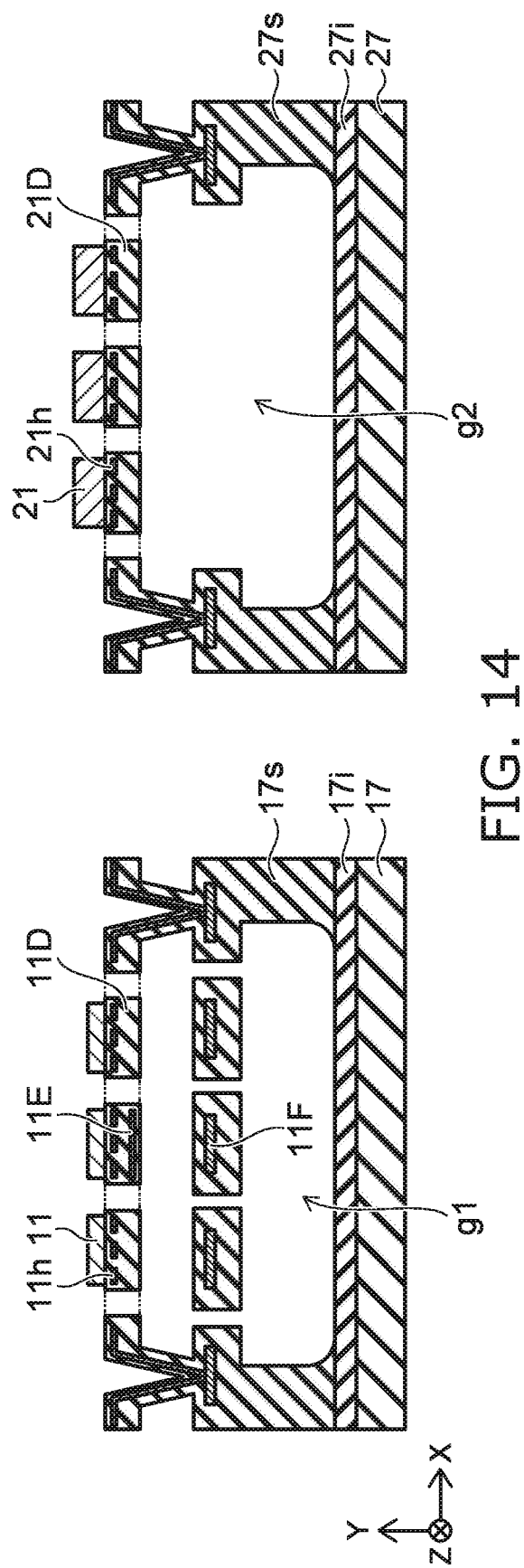
FIG. 14 is a schematic cross-sectional view illustrating the method for manufacturing the sensor according to the third embodiment.

FIG. 13A, FIG. 13B, and FIG. 14 are schematic cross-sectional views illustrating the method for manufacturing the sensor according to the third embodiment.

As shown in FIG. 13A, a sacrificial layer 31 is formed on a portion of an insulating film 18i provided on a substrate 18. The film portion 11D that includes the heater 11h is formed on the sacrificial layer 31. The film portion 11D is continuous with a supporter 18s provided on the insulating film 18i. A sacrificial layer 32 is formed on another portion of the insulating film 18i. The structure portion 21D that includes the heater 21h is formed on the sacrificial layer 32. The structure portion 21D that includes the heater 21h is continuous with the supporter 18s. For example, the formation of the sacrificial layer 32 may be simultaneously performed with the formation of the sacrificial layer 31. The formation of the structure portion 21D may be simultaneously performed with the formation of the film portion 11D.

As shown in FIG. 13B, portions of the substrate 18, the insulating film 18i, and the supporter 18s are divided. Thereby, the substrate 17, the insulating film 17i, and the supporter 17s are obtained. The substrate 27, the insulating film 27i, and the supporter 27s are obtained. The first film 11 is formed on the film portion 11D. The second film 21 is formed on the structure portion 21D including the heater 21h. For example, sputtering or the like is used to form the first film 11 and the second film 21.

For example, the formation conditions of the first film 11 are different from the formation conditions of the second film 21. For example, the material (e.g., the composition) of the first film 11 is different from the material (e.g., the composition) of the second film 21. Thereby, for example, the second film 21 includes at least one of the second density that is greater than the first density of the first film, or the second concentration of the first element that is greater than the first concentration of the first film 11.

The sacrificial layer 31 and the sacrificial layer 32 are removed as shown in FIG. 14. For example, the sacrificial layer 31 and the sacrificial layer 32 are removed by ashing, etc. A MEMS structure is obtained thereby. The sensor according to the first embodiment is obtained thereby. For example, the sensor 110, etc., are obtained by the method illustrated in FIG. 13A, FIG. 13B, and FIG. 14.

FIG. 15A, FIG. 15B, FIG. 16A, and FIG. 16B are schematic cross-sectional views illustrating a method for manufacturing the sensor according to the third embodiment.

As shown in FIG. 15A, the sacrificial layer 31 is formed on a portion of the insulating film 17i provided on the substrate 17. The film portion 11D that includes the heater 11h is formed on the sacrificial layer 31. The film portion 11D is continuous with the supporter 17s provided on the insulating film 17i. The sacrificial layer 32 is formed on another portion of the insulating film 17i. The structure portion 21D that includes the heater 21h is formed on the sacrificial layer 32. The structure portion 21D that includes the heater 21h is continuous with the supporter 17s provided on the insulating film 17i. For example, the formation of the sacrificial layer 32 may be simultaneously performed with the formation of the sacrificial layer 31. The formation of the structure portion 21D may be simultaneously performed with the formation of the film portion 11D.

As shown in FIG. 15B, a mask 20M is formed on the structure portion 21D including the heater 21h. The first film 11 is formed on the film portion 11D in this state. Subsequently, the mask 20M is removed.

Figure 16A:
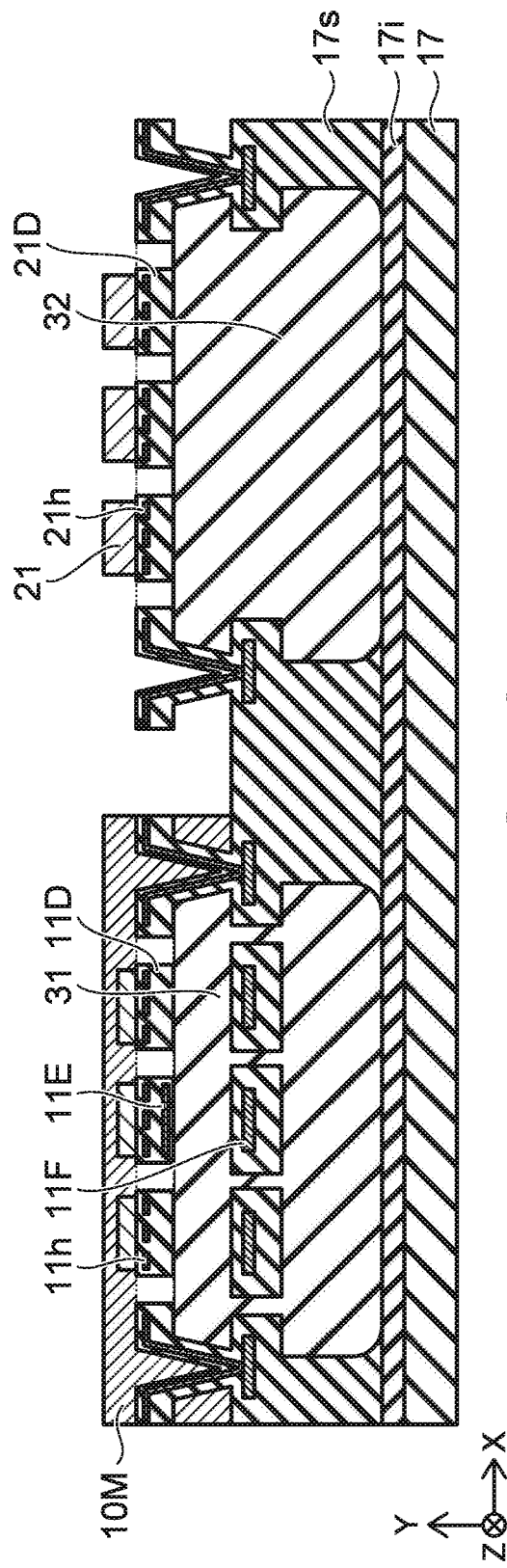
FIG. 16A and FIG. 16B are schematic cross-sectional views illustrating a method for manufacturing the sensor according to the third embodiment.

As shown in FIG. 16A, a mask 10M is formed on the film portion 11D and the first film 11. The second film 21 is formed on the structure portion 21D including the heater 21h in this state.

For example, the formation conditions of the first film 11 are different from the formation conditions of the second film 21. For example, the material (e.g., the composition) of the first film 11 is different from the material (e.g., the composition) of the second film 21. Thereby, for example, the second film 21 includes at least one of the second density that is greater than the first density of the first film, or the second concentration of the first element that is greater than the first concentration of the first film 11. The mask 10M is removed after forming the second film 21.

Figure 16B:
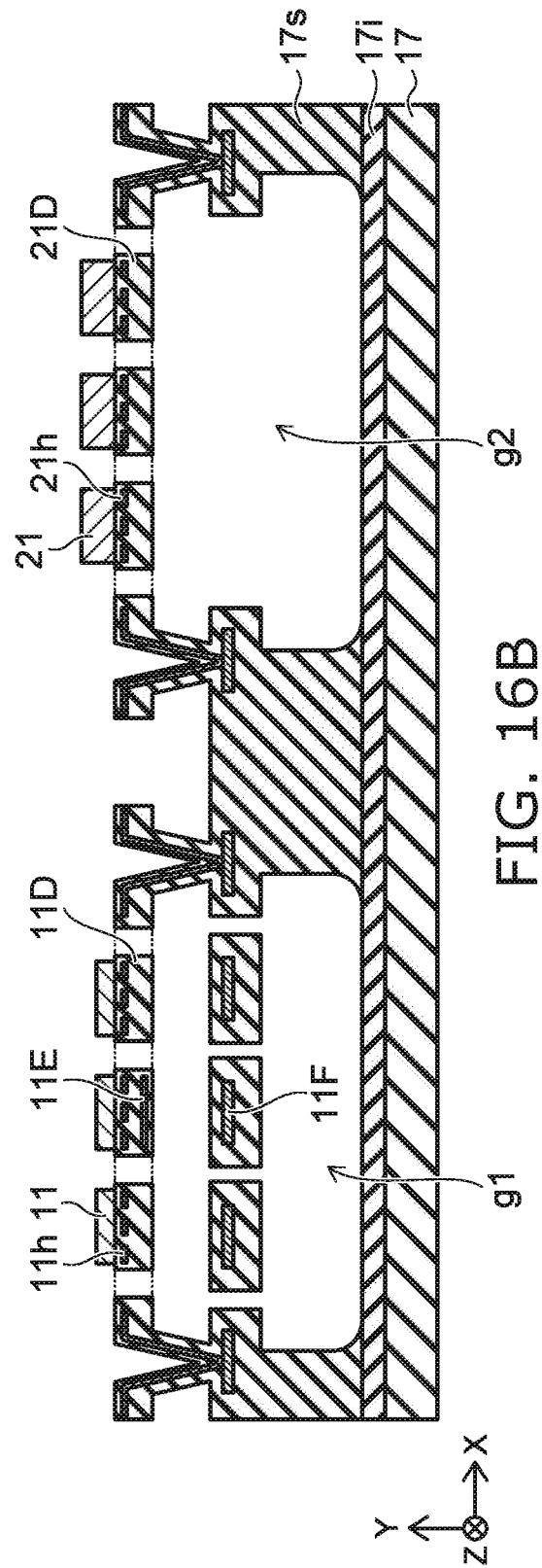

The sacrificial layer 31 and the sacrificial layer 32 are removed as shown in FIG. 16B. For example, the sacrificial layer 31 and the sacrificial layer 32 are removed by ashing, etc. A MEMS structure is obtained thereby. The sensor according to the first embodiment is obtained thereby. For example, the sensor 140 can be provided by the method illustrated in FIG. 15A, FIG. 15B, FIG. 16A, and FIG. 16B.

In the description recited above, the sequence of the process illustrated in FIG. 15B and the process illustrated in FIG. 16A is interchangeable.

For example, the substrate 17, the substrate 18, and the substrate 27 include silicon. For example, the insulating film 17i, the insulating film 18i, and the insulating film 27i include silicon oxide. The silicon oxide may include, for example, a thermal oxide film of silicon. The supporter 17s, the supporter 18s, and the supporter 27s include silicon nitride. For example, the insulating portion that is included in the film portion 11D and the structure portion 21D includes silicon nitride. Various modifications of these materials are possible.

For example, the first element may be hydrogen. For example, there is a possibility of an explosion occurring when the concentration of hydrogen in ambient air is not less than 4% and not more than 75%. To safely utilize hydrogen, it is desirable for the sensor to promptly detect a hydrogen leak. By regularly calibrating the hydrogen sensor, normal operations of the hydrogen sensor can be maintained. In the normal state of use of the hydrogen sensor, there are many cases where the concentration of hydrogen is extremely low in the environment in which the hydrogen sensor is placed. In the normal state of use of the hydrogen sensor, there are many cases where it is difficult to perform the calibration by supplying hydrogen to the hydrogen sensor.

For example, when a hydrogen sensor is provided in a hydrogen pipeline, etc., there are also cases where it is difficult for the operator to approach the hydrogen sensor. For example, when a fuel cell is provided in the automobile, etc., there are also cases where it is difficult for the operator to approach the hydrogen sensor detecting the leakage of hydrogen from the fuel cell. For example, technology in which it is possible to calibrate the hydrogen sensor by a remote operation or the like is desirable.

In the sensor according to the embodiment, the sensor part 10 that detects the first element to be detected is provided, and the structure body 20 that includes the second film 21 that can release the first element in the calibration operation is provided. The structure body 20 functions as a first element-including outgassing device. For example, the first element (e.g., hydrogen) is pre-introduced to the second film 21. For example, the first element (e.g., hydrogen) is released from the second film 21 by the heater 21h heating the second film 21.

For example, the calibration of the hydrogen sensor can be performed using the concentration of hydrogen obtained based on the volume in the package of the hydrogen sensor and the amount of the hydrogen included in the second film 21.

For example, at a low temperature (e.g., room temperature or the like), the hydrogen can be absorbed or released substantially without hysteresis in the first film 11 included in the sensor part 10. The second film 21 that is included in the structure body 20 releases hydrogen at a high temperature. For example, the heater 11h that is provided in the sensor part 10 and the heater 21h that is included in the structure body 20 are controlled independently. In the calibration operation, the temperature of the second film 21 is set to be greater than the temperature of the first film 11.

For example, it is favorable for the size (e.g., the surface area) of the second film 21 to be not less than 0.5 times the size (e.g., the surface area) of the first film 11. Thereby, for example, about 1000 ppm of hydrogen can be released from the second film 21. The amount of the hydrogen released from the second film 21 can be increased by making the second film 21 thicker.

According to the embodiments, for example, the calibration of the sensor is possible by using a remote operation. For example, the calibration of the sensor is possible without an operation of the operator.

The embodiments may include the following configurations (e.g., technological proposals).

Configuration 1

A sensor, comprising:
 a sensor part including a first film; and
 a structure body including a second film,
 the first film having a first density, and a first concentration of a first element,
 the second film having at least one of a second density, or a second concentration of the first element, the second concentration being greater than the first concentration, the second density being greater than the first density.

Configuration 2

The sensor according to Configuration 1, further comprising:
 a first member; and
 a second member including a hole,
 the sensor part and the structure body being provided between the first member and the second member,
 a distance between the hole and the sensor part being less than a distance between the hole and the structure body.

Configuration 3

The sensor according to Configuration 2, wherein
 the first member includes a first surface facing the second member, and
 the sensor part and the structure body are provided at the first surface.

Configuration 4

The sensor according to Configuration 1, further comprising:
 a first member including a first surface; and
 a second member including a second surface facing the first surface,
 the second member including a hole,
 the structure body being provided at the second surface,
 the sensor part being provided at the first surface.

Configuration 5

The sensor according to Configuration 4, wherein
 the sensor part overlaps the hole in a direction from the first member toward the second member, and
 the structure body does not overlap the hole in the direction.

Configuration 6

The sensor according to any one of Configurations 2 to 5, wherein
 at least one of the first member or the second member includes a side portion, and
 at least a portion of the structure body is between the sensor part and the side portion.

Configuration 7

The sensor according to any one of Configurations 1 to 6, wherein
 at least a portion of the sensor part is between a portion of the structure body and an other portion of the structure body.

Configuration 8
The sensor according to any one of Configurations 1 to 6, comprising:
a plurality of the structure bodies,
the plurality of structure bodies including a first structure body and a second structure body,
at least a portion of the sensor part being between the first structure body and the second structure body.

Configuration 9
The sensor according to Configuration 8, wherein
the plurality of structure bodies further includes a third structure body and a fourth structure body, and
at least a portion of the sensor part is between the third structure body and the fourth structure body in a direction crossing a direction from the first structure body toward the second structure body.

Configuration 10
The sensor according to any one of Configurations 1 to 9, wherein
the first film includes a second element and a third element,
the second element includes at least one selected from the group consisting of Pd, Pt, and Au, and
the third element includes at least one selected from the group consisting of Si, P, and B.

Configuration 11
The sensor according to Configuration 10, wherein
the first film further includes a fourth element, and
the fourth element includes at least one selected from the group consisting of Cu, Ag, Ni, Fe, and Cr.

Configuration 12
The sensor according to any one of Configurations 1 to 11, wherein
the first film is amorphous and the second film includes a crystal, or
the second film has a higher crystallinity than a crystallinity of the first film.

Configuration 13
The sensor according to any one of Configurations 1 to 12, wherein
a sensor signal output from the sensor part changes according to a concentration of the first element included in a gas at a periphery of the sensor part.

Configuration 14
The sensor according to any one of Configurations 1 to 13, wherein
the structure body includes a heater.

Configuration 15
The sensor according to Configuration 14, further comprising:
a controller,
the controller including a heater circuit electrically connected to the heater,
the heater circuit being configured to supply a current to the heater,
the second film releasing the first element when a current is supplied to the heater.

Configuration 16
The sensor according to Configuration 15, wherein the sensor part includes a first electrode and a second electrode,
the controller includes a detection circuit electrically connected to the first and second electrodes,
the detection circuit is configured to output a detection signal, and
the detection signal changes according to a concentration of the first element included in a gas at a periphery of the sensor part.

Configuration 17
The sensor according to Configuration 16, wherein a distance between the first electrode and the second electrode changes according to the concentration of the first element included in the gas at the periphery of the sensor part.

Configuration 18
The sensor according to Configuration 16 or 17, wherein
the controller includes a control circuit, and
the control circuit causes the detection signal to be output from the detection circuit by calibrating a signal obtained from the first and second electrodes when the first element is released.

Configuration 19
A method for calibrating a sensor,
the sensor including
a sensor part including a first film, and
a structure body including a second film,
the first film having a first density, and a first concentration of a first element,
the second film having at least one of a second density, or a second concentration of the first element, the second concentration being greater than the first concentration, the second density being greater than the first density,
the method comprising:
causing the first element to be released from the second film of the sensor; and
calibrating an output obtained from the sensor part when the first element is released.

According to the embodiments, a sensor and a method for calibrating a sensor can be provided in which stable detection accuracy can be easily obtained.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in sensors such as sensor parts, first films, electrodes, second films, heaters, first members, second members, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all sensors, and methods for calibrating sensors practicable by an appropriate design modification by one skilled in the art based on the sensors, and the methods for calibrating sensors described above as embodiments of the invention also are within the scope of the invention to the extent that the purport of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A sensor, comprising:
a sensor part including a first film;
a structure body including a second film;
a first member including a first surface; and
a second member including a second surface facing the first surface,
the first film having a first density,
the second film having a second density being greater than the first density,
the second member including a hole,
the structure body being provided at the second surface,
the sensor part being provided at the first surface,
wherein
the sensor part overlaps the hole in a direction from the first member toward the second member, and
the structure body does not overlap the hole in the direction.

2. The sensor according to claim 1, wherein
at least one of the first member or the second member includes a side portion, and
at least a portion of the structure body is between the sensor part and the side portion.

3. The sensor according to claim 1, wherein
at least a portion of the sensor part is between a portion of the structure body and an other portion of the structure body.

4. The sensor according to claim 1, comprising:
a plurality of the structure bodies,
the plurality of structure bodies including a first structure body and a second structure body,
at least a portion of the sensor part being between the first structure body and the second structure body.

5. The sensor according to claim 4, wherein
the plurality of structure bodies further includes a third structure body and a fourth structure body, and
at least a portion of the sensor part is between the third structure body and the fourth structure body in a direction crossing a direction from the first structure body toward the second structure body.

6. The sensor according to claim 1, wherein
the first film includes a second element and a third element,
the second element includes at least one selected from the group consisting of Pd, Pt, and Au, and
the third element includes at least one selected from the group consisting of Si, P, and B.

7. The sensor according to claim 6, wherein
the first film further includes a fourth element, and
the fourth element includes at least one selected from the group consisting of Cu, Ag, Ni, Fe, and Cr.

8. The sensor according to claim 1, wherein
the first film is amorphous and the second film includes a crystal, or
the second film has a higher crystallinity than a crystallinity of the first film.

9. The sensor according to claim 1, wherein
a sensor signal output from the sensor part changes according to a concentration of the first element included in a gas at a periphery of the sensor part.

10. The sensor according to claim 1, wherein
the structure body includes a heater.

11. The sensor according to claim 10, further comprising:
a controller,
the controller including a heater circuit electrically connected to the heater,
the heater circuit being configured to supply a current to the heater,
the second film releasing the first element when a current is supplied to the heater.

12. The sensor according to claim 11, wherein
the sensor part includes a first electrode and a second electrode,
the controller includes a detection circuit electrically connected to the first and second electrodes,
the detection circuit is configured to output a detection signal, and
the detection signal changes according to a concentration of the first element included in a gas at a periphery of the sensor part.

13. The sensor according to claim 12, wherein
a distance between the first electrode and the second electrode changes according to the concentration of the first element included in the gas at the periphery of the sensor part.

14. The sensor according to claim 12, wherein
the controller includes a control circuit, and
the control circuit causes the detection signal to be output from the detection circuit by calibrating a signal obtained from the first and second electrodes when the first element is released.

15. A sensor, comprising:
a sensor part including a first film;
a structure body including a second film;
a first member; and
a second member including a hole,
the first film having a first density,
the second film having a second density being greater than the first density,
the sensor part and the structure body being provided between the first member and the second member,
a direction from the sensor part to the hole crossing a direction from the sensor part to the structure body, and
a distance between the hole and the sensor part being less than a distance between the hole and the structure body.

* * * * *